(12) United States Patent
Lin

(10) Patent No.: US 11,712,293 B2
(45) Date of Patent: Aug. 1, 2023

(54) RESECTOSCOPE OPERATING HANDLE AND ELECTRODE FITTING STRUCTURE AND FITTING METHOD

(71) Applicant: SIMAI CO., LTD., Guangdong (CN)

(72) Inventor: Min Lin, Guangdong (CN)

(73) Assignee: SIMAI CO., LTD., Zhuhai (CN)

( * ) Notice: Subject to any disclaimer, the term of this patent is extended or adjusted under 35 U.S.C. 154(b) by 531 days.

(21) Appl. No.: 16/886,768

(22) Filed: May 28, 2020

(65) Prior Publication Data

US 2020/0375652 A1 Dec. 3, 2020

(30) Foreign Application Priority Data

May 31, 2019 (CN) .......................... 201910466845.2

(51) Int. Cl.
*A61B 18/14* (2006.01)
*A61B 17/00* (2006.01)
*A61B 18/00* (2006.01)

(52) U.S. Cl.
CPC .. *A61B 18/149* (2013.01); *A61B 2017/00438* (2013.01); *A61B 2018/0091* (2013.01); *A61B 2018/00172* (2013.01); *A61B 2018/00196* (2013.01); *A61B 2018/00601* (2013.01); *A61B 2018/00607* (2013.01); *A61B 2018/00982* (2013.01)

(58) Field of Classification Search
CPC ... A61B 18/149; A61B 18/14; A61B 18/1445; A61B 18/1492; A61B 18/1815; A61B 18/1442; A61B 2018/1475; A61B 2018/00601; A61B 2018/00952; A61B 2018/00172; A61B 2018/00196; A61B 2018/0091; A61B 2018/00982; A61B 2018/1455; A61B 2018/1407; A61B 2017/00075; A61B 2017/0046; A61B 2017/00477; A61B 2017/320016
See application file for complete search history.

(56) References Cited

U.S. PATENT DOCUMENTS

| 4,744,361 | A | * | 5/1988 | Karasawa | .......... | A61B 1/00137 |
| | | | | | | 600/105 |
| 4,994,062 | A | * | 2/1991 | Nishigaki | ............ | A61B 18/149 |
| | | | | | | 606/46 |
| 2011/0295066 | A1 | * | 12/2011 | Fan | .................... | A61B 1/00128 |
| | | | | | | 600/156 |

FOREIGN PATENT DOCUMENTS

| CN | 201529144 U | 7/2010 |
| CN | 206950221 U | 2/2018 |

* cited by examiner

*Primary Examiner* — Joseph A Stoklosa
*Assistant Examiner* — Marina Delaney Templeton

(57) ABSTRACT

A resectoscope operating handle and electrode fitting structure and fitting method are provided. The fitting structure includes a slider of a resectoscope operating handle and a binding post of an electrode. The slider has a front surface and a back surface. The front surface of the slider is provided with a mounting groove for mounting the binding post. An end surface of the binding post is perpendicular to the front surface of the slider. The binding post is mounted in the mounting groove, and an axial direction of the binding post is perpendicular to a plane where the handle is located. The resectoscope operating handle and electrode fitting structure and fitting method of the present invention can ensure that an electrode is accurately and firmly fixed to an operating handle under the condition of convenience in operation.

12 Claims, 4 Drawing Sheets

RESECTOSCOPE OPERATING HANDLE AND ELECTRODE FITTING STRUCTURE AND FITTING METHOD

CROSS REFERENCE TO RELATED APPLICATIONS

The present application claims the benefit of Chinese Patent Application No. 201910466845.2 filed on May 31, 2019, the contents of which are incorporated herein by reference in their entirety.

TECHNICAL FIELD

The present invention relates to the technical field of medical equipment, and more particularly, to a resectoscope operating handle and electrode fitting structure and fitting method.

BACKGROUND

A resectoscope is a commonly used instrument in electrosurgery, can be used in conjunction with an electrode, and is widely used in electrosurgical minimally invasive hand therapy in urology. A general resectoscope includes an outer sheath, an inner sheath, an endoscope, and an operating handle. The operating handle is an operator capable of connecting the inner sheath and the endoscope and mounting an electrode. During the surgery, medical staff can hold the operating handle in hand, and push a slider on the handle with the thumb to control the position of the electrode to cut and coagulate the tissue.

The Chinese patent document with application number 200920054446.7 discloses a plasma bipolar resectoscope. A fixing mode of an operating handle and an electrode is: forming a through hole on a slider, designing a cylindrical binding post of the electrode, and inserting the electrode into the through hole of the slider to form a clearance fit between a hole and a shaft. After assembly by this method, there is no axial positioning between the binding post and the slider, and the binding post may be moved axially, so this method has the disadvantages of insufficient constraint, unstable positioning, and electrode shift during actual use.

The Chinese patent document with application number 201621377326.7 discloses a slider assembly of a resectoscope handle in a bipolar resectoscope. A movable snap structure is designed on a slider on an operating handle. The movable snap structure includes a positioning block, a spring, a steel ball, a guide positioning block, a spring clamping seat, and an ejector rod. An inclined slider structure is arranged between the ejector rod and the spring clamping seat. A bevel groove is designed on two electrode tubes of an electrode. The electrode tubes are inserted along holes on the slider, and then the ejector rod is pressed, so that the spring clamping seat clamps the bevel groove on the electrode tubes to fix the electrode. In this solution, there are many structural parts on the slider, and the processing and assembly process of each part is cumbersome. In addition, the wall of the electrode tube is thin, and it is difficult to open the bevel on the wall of the tube. Besides, a high-frequency connecting wire is separated from the electrode. The connection of the high-frequency connecting wire with the electrode during use has the risks of electric leakage and poor contact. Therefore, the structure of this solution is more complicated, the manufacturing process is highly required, and the operation of mounting and dismounting the electrode is inconvenient.

On the other hand, a connection relationship between an inner sheath, an endoscope and an operating handle is that: a proximal end of the operating handle is connected to a proximal end of the endoscope, and a distal end of the operating handle is a handle locking head used for being locked with a proximal end of the inner sheath. In order to prevent an electrolyte from flowing back to the handle during the surgery, a joint between the handle locking head and the inner sheath is sealed with a sealing plug. Specifically, a notch is provided on a side wall of the handle locking head, an electrode rod is sleeved with a soft elastic sealing plug which matches the notch of the handle locking head, and when the electrode and the handle are mounted together, the sealing plug fills the notch of the handle locking head, so that an outer surface of the handle locking head is continuous and smooth, the electrode rod is radially fixed on the handle, and the elastic characteristics of the sealing plug are used to realize the relative sealing of the handle and the electrode part. However, the sealing structure has the following disadvantages: due to the small contact area between the handle locking head and the sealing plug, the fit therebetween is unstable, resulting in that the relative fixation of the endoscope and the electrode and the relative fixation of the electrode and the handle are unstable. Moreover, because the handle locking head is made of a rigid material and the sealing plug is made of a soft elastic material, the degree of wear of the handle locking head and the sealing plug is different, there may be a clearance therebetween or poor contact, resulting in bad sealing performance. In addition, the outer side surface of the handle locking head is rigid and cannot be deformed, and there may be a clearance when fitting a rigid inner sheath, thereby resulting in the bad sealing performance.

SUMMARY

In view of the problems existing in the conventional art, the present invention provides a resectoscope operating handle and electrode fitting structure. The fitting structure can ensure good operability and make the fit between an electrode and an operating handle more reliable.

To achieve the above object, the present invention adopts the following technical solutions:

A resectoscope operating handle and electrode fitting structure includes a slider of a resectoscope operating handle and a binding post of an electrode.

The slider has a front surface and a back surface. The front surface and the back surface correspond to the inside and outside of a user, respectively. The front surface of the slider is provided with a mounting groove for mounting the binding post. An end surface of the binding post is perpendicular to the front surface of the slider. The binding post is mounted in the mounting groove, and an axial direction of the binding post is perpendicular to a plane where the handle is located.

Preferably, the mounting groove is a U-shaped groove, an opening of the U-shaped groove penetrates a left side surface of the slider, a lower portion of the U-shaped groove has a notch penetrating the slider, an inner groove wall of the U-shaped groove is provided with a C-shaped groove concaved inwardly, and an arc-shaped groove is provided at an intersection of the lower right of the inner groove wall of the U-shaped groove and the front surface of the slider.

The slider is fixed to one end of a connecting bridge of the resectoscope operating handle, and a support rod of the resectoscope operating handle passes through the slider.

The binding post includes a post cover, an inner shell and an outer shell. The inner shell is used for allowing a cable to pass through. The post cover is connected to the bottom of the inner shell. The outer shell is sleeved outside the inner shell. The outer shell and the inner shell form a housing assembly. The housing assembly is provided with a first limiting mechanism for limiting the axial movement of the outer shell and the inner shell and a second limiting mechanism for limiting the circumferential rotation of the inner shell, so that the outer shell is rotatable forwardly and reversely around the inner shell.

An annular shoulder is arranged at the bottom of the outer shell, and the annular shoulder is provided with a limiting boss protruding outward.

The binding post may be embedded in the slider along the U-shaped groove. When the outer shell is rotated, the limiting boss can abut against an end surface of the arc-shaped groove, and the annular shoulder can be screwed into the C-shaped groove, so that the electrode is constrained on the slider, and the degrees of freedom in other directions are limited except for the rotation of the outer shell as an axis.

Preferably, the arc-shaped groove is a ¼ circular groove, that is, the arc shape of the arc-shaped groove is 90°.

Preferably, the first limiting mechanism includes an annular rib arranged on an outer wall of the inner shell.

Preferably, the second limiting mechanism includes a positioning protrusion arranged on the top of the inner shell and extending along the axial direction of the inner shell, and a positioning hole provided on a top inner wall of the outer shell and corresponding to the positioning protrusion.

Preferably, the bottom of the inner shell is provided with a base having an annular protrusion, and the annular shoulder abuts against an upper end of the base.

Preferably, opposite sides of the outer shell have mutually parallel planes, and the planes extend from a top end of the outer shell to a bottom end of the annular shoulder.

Preferably, the electrode includes a binding post, an electrode rod and a high-frequency connecting wire, the high-frequency connecting wire is welded to the electrode rod and fixed in the inner shell, the inner shell is filled with epoxy resin glue, the post cover seals the inner shell, and the outer shell is sleeved and fixed on the inner shell.

Preferably, the fitting structure further includes a sealing plug made of a soft elastic material, a distal end of the operating handle has a handle locking head for being fixed with a proximal end of an inner sheath, a proximal end of the operating handle is used to connect a proximal end of a rod portion of an endoscope, a distal end of the rod portion of the endoscope extends in the direction of the electrode, and the sealing plug is arranged between the proximal end of the inner sheath and the handle locking head.

Preferably, the sealing plug is cylindrical, the sealing plug is provided with two through holes in the axial direction, each through hole is used for allowing the rod portion of the endoscope and the electrode rod of the electrode to pass through, the proximal end of the inner sheath is provided with a limiting surface for abutting against a distal end of the sealing plug, a side wall of the proximal end of the inner sheath wraps the sealing plug and is fixedly connected to the handle locking head, and a proximal end of the sealing plug abuts against the handle locking head.

Preferably, the sealing plug and the inner sheath are in interference fit, after the proximal end of the inner sheath and the handle locking head are tightly connected, the sealing plug is compressed and deformed and closely fits an inner wall of the proximal end of the inner sheath, and there is no clearance therebetween.

Preferably, the bottom surface of the sealing plug is further provided with a protrusion, and the protrusion can be inserted into a notch on a side wall of the handle locking head and can circumferentially position the sealing plug.

The present invention also provides a fitting method of the fitting structure, which includes the following steps.

A, During mounting, an end portion of a binding post is pushed to an inner end of a U-shaped groove along the U-shaped groove, and then an outer shell of the binding post is rotated clockwise until the outer shell cannot be rotated, so that an electrode and a slider are locked.

B, During dismounting, the outer shell of the binding post is rotated counterclockwise until the outer shell cannot be rotated, and the binding post is pushed out along the U-shaped groove, so that the constraint between the electrode and the slider is released.

Compared with the conventional art, the present invention has the following advantages.

1. An outer shell of a binding post of the present invention is provided with a shoulder, a slider is provided with a C-shaped groove, the shoulder on the outer shell is rotated into the C-shaped groove by rotation, the upper and lower surfaces of the shoulder completely fit the upper and lower surfaces of the C-shaped groove, a side wall of the shoulder completely fits a side wall of the C-shaped groove, and the degree of freedom of the binding post in an axial direction and a plane direction are limited, thereby ensuring the stable position between the electrode and the slider.

2. There are no extra parts on the slider of the present invention, only two grooved structures need to be processed on the slider, a corresponding limiting structure is provided on an electrode binding post, and the components of the binding post are injection-molded. A high-frequency connecting wire and the electrode may also be integrated, which simplifies the processing technology.

3. The binding post of the present invention is located on one side of an operating handle in a manner perpendicular to a plane where the operating handle is located. It is more convenient to mount from the side and is easier to operate. It is possible to avoid interference between an electrode cable and the operating hand of a doctor during the surgical operation, and avoid problem of operation hindering.

4. A sealing plug of the present invention forms a sealing layer between a handle locking head and an end surface of an inner sheath, the material of the sealing layer is uniform, and there is no internal clearance. The binding post is mounted after being compressed and deformed by the handle locking head and the inner sheath. The sealing performance is better. The design of a protrusion on the sealing plug can not only adapt to the handle locking head of the conventional art, but also achieve the circumferential positioning of the sealing plug to avoid its rotation affecting the sealing performance and achieve a good sealing function.

DETAILED DESCRIPTION OF THE EMBODIMENTS

The present embodiment provides a resectoscope operating handle and electrode fitting structure.

Figure 1:
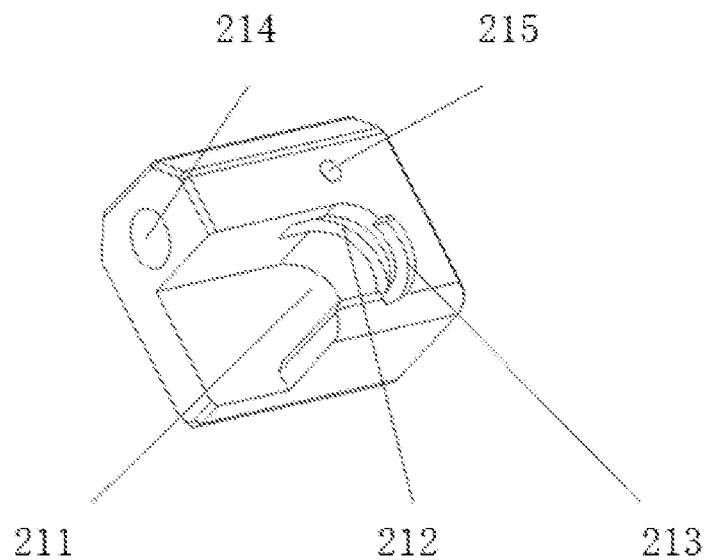
FIG. 1 is a structural view of a slider on an operating handle.
Figure 3:
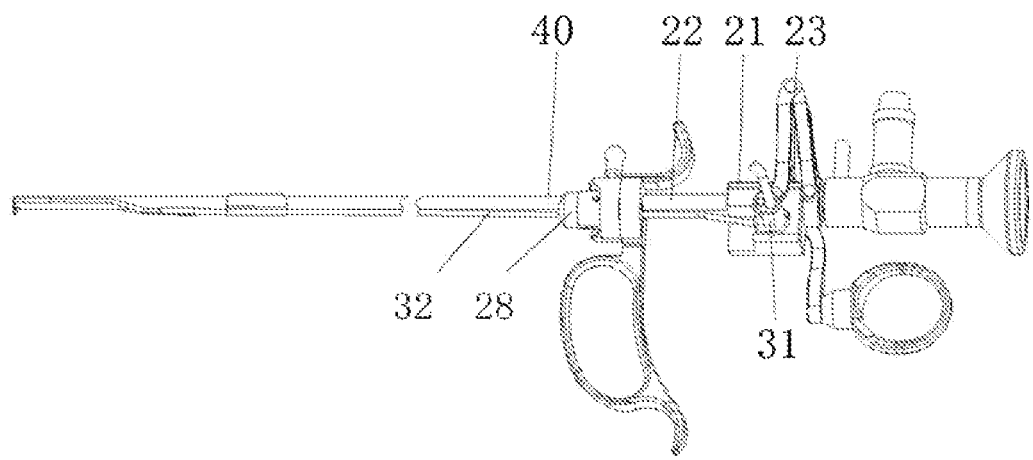
FIG. 3 is an assembly view of a resectoscope operating handle and an electrode.
Figure 4:
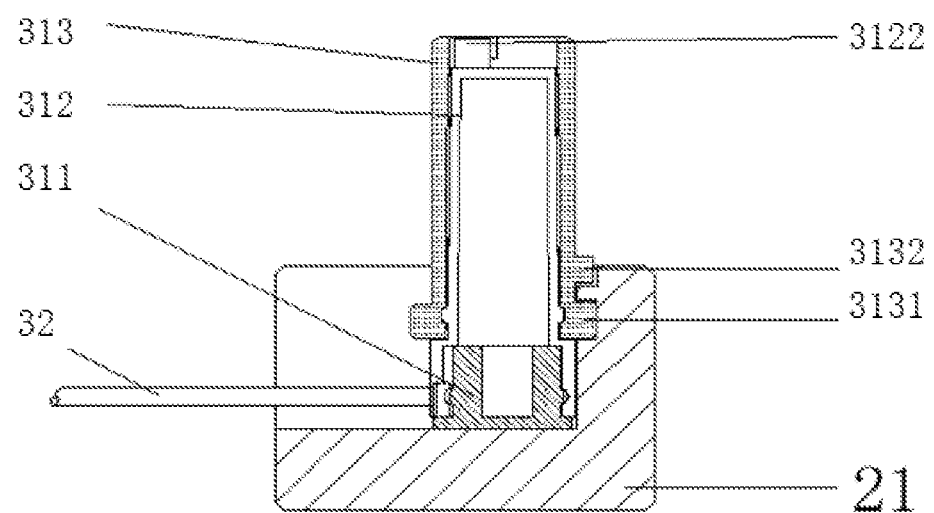
FIG. 4 is a cross-sectional view of fitting a slider and a binding post.
Figure 5:
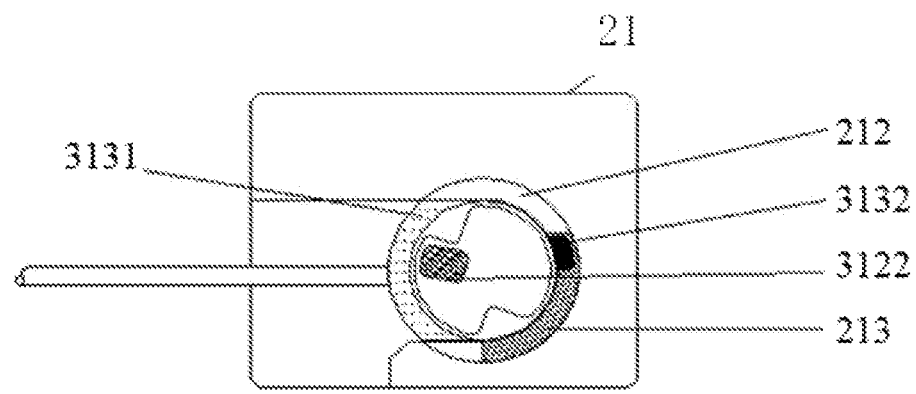
FIG. 5 is a cross-sectional view of fitting a slider and a binding post from another perspective.
Figure 6:
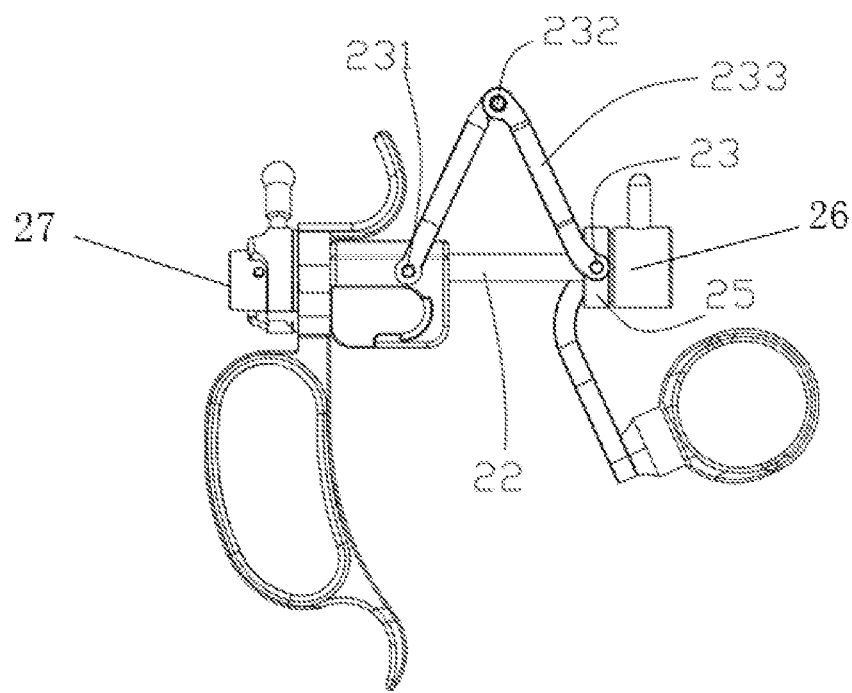
FIG. 6 is a schematic stereostructure view of an operating handle.

Referring to FIG. 1, FIG. 3 and FIG. 6, a slider 21 belongs to a part of the resectoscope operating handle, which serves to fix an electrode and drive the electrode to slide back and forth. A surface opposite to an operator when the resectoscope operating handle is used is defined as a front surface. The slider 21 has a total of six surfaces: a front surface, a back surface, a left side surface, a right side surface, a top surface, and a bottom surface. A through hole penetrates the left side surface and the right side surface, which is a support rod passing hole 214. The front surface of the slider 21 is provided with a screw fixing hole 215. Meanwhile, the slider 21 is provided with a U-shaped groove 211. The U-shaped groove 211 is concaved inwardly from the front surface of the slider 21 to form a groove with a flat bottom surface. A left end of the U-shaped groove 211 penetrates the left side surface of the slider 21. A lower portion of the U-shaped groove 211 penetrates the bottom surface of the slider 21 to form a notch. An inner groove wall of the U-shaped groove 211 is provided with a C-shaped groove 212 concaved inwardly. An intersection between the lower right of the inner groove wall of the U-shaped groove 211 and the front surface of the slider 21 is provided with a ¼ circular groove 213. The upper end surface and the lower end surface of the U-shaped groove 211 are parallel to each other.

The slider 21 is fixed to a connecting bridge 23 of the resectoscope operating handle through the screw fixing hole 215. The support rod passing hole 214 fits a support rod 22 of the resectoscope operating handle. The connecting bridge 23 is a connecting rod mechanism. The slider 21 may be driven by a finger force to move back and forth along the support rod 22. Specifically, as shown in FIG. 6, the connecting bridge 23 is provided with three nodes, a left end node 231 is used to connect with the slider 21, a right end node 233 is mounted on a fixed ring 25, the fixed ring 25 is fixed on the support rod 22, and a middle node 232 is provided with a torsion spring for resetting.

Figure 2:
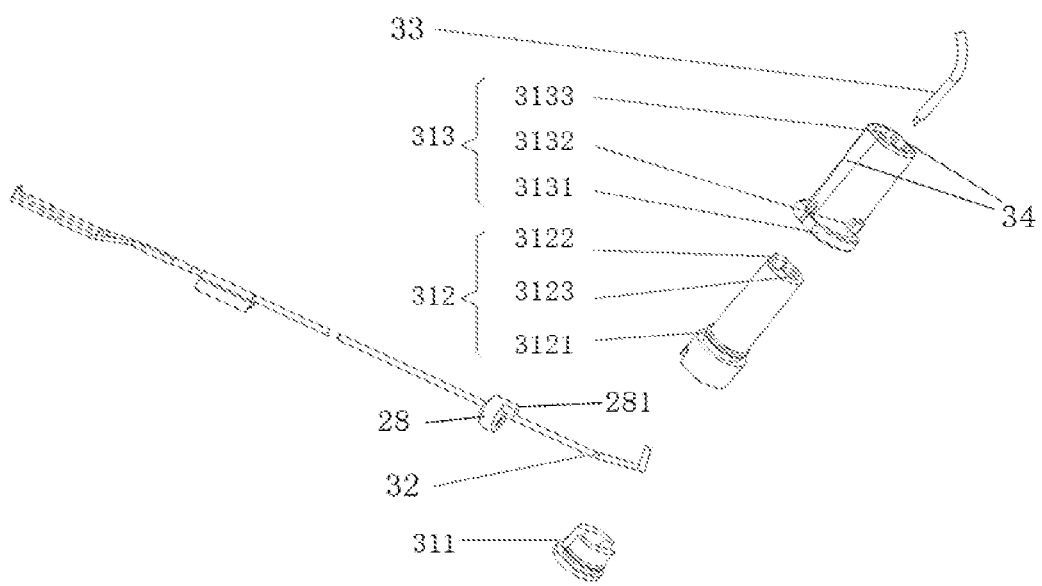
FIG. 2 is an exploded view of an electrode.

Referring to FIG. 2 and FIG. 3, the electrode of the present embodiment includes a binding post 31, an electrode rod 32 and a high-frequency connecting wire 33. The binding post 31 includes a post cover 311, an inner shell 312 and an outer shell 313. The inner shell 312 and the outer shell 313 are in a cylindrical shape. The inner shell 312 penetrates up and down, the through hole is a wire through hole 3123, the bottom of the inner shell 312 is provided with a base having an annular protrusion, an outer wall of the inner shell 312 is provided with an annular rib 3121, the annular rib 3121 is adjacent to the base, and a positioning protrusion 3122 extending along the axial direction of the inner shell 312 is arranged on the top of the inner shell 312. The outer shell 313 is cylindrical and penetrates up and down, the bottom thereof is provided with an annular shoulder 3131 protruding outward, and the annular shoulder 3131 functions as a bayonet. A limiting boss 3132 is arranged on the outer wall of the outer shell 313, and a special-shaped hole 3133 corresponding to the positioning protrusion 3122 is provided on the top of the inner wall of the outer shell 313. The post cover 311 fits the bottom of the inner shell 312, the outer shell 313 is sleeved outside the inner shell 312, and the annular shoulder 3131 of the outer shell 313 abuts against an upper end of the base of the inner shell 312. The two opposite side walls of the outer shell 313 have two planes 34 parallel to each other. The two planes 34 extend from the bottom of the outer shell to the top of the outer shell. The spacing between the two planes 34 matches the spacing between the upper and lower end surfaces of the U-shaped groove 211, so that the two parallel planes 34 of the outer shell 313 facilitate entry between the upper and lower end surfaces of the U-shaped groove 211.

The high-frequency connecting wire 33 and the electrode rod 32 are welded together and fixed in the inner shell 312, the inner shell is filled with epoxy resin glue, the post cover 311 seals the inner shell 312, and the outer shell 313 is sleeved and fixed on the inner shell 312. Through the annular rib 3121, the axial movement of the inner shell 312 is limited, and the positioning protrusion 3122 passes through the special-shaped hole 3133 to achieve the circumferential positioning of the inner shell 312, so that the outer shell 313 may rotate forwardly and reversely for 90 degrees by using the inner shell 312 as an axis.

Referring to FIG. 3, during the mounting process of the electrode and the resectoscope operating handle, the binding post 31 of the electrode is first fixed to the slider 21 and then fixed to an endoscope 40. During the dismounting process, the binding post 31 of the electrode is first separated from the slider 21 and then separated from the endoscope 40.

Specifically, referring to FIG. 1 to FIG. 6, in the process of mounting the electrode on the resectoscope operating handle, first, the end of the binding post 31 is vertically opposed to the front surface of the slider 21, two parallel planes 34 of the outer shell 313 of the binding post 31 are rotated to a horizontal direction, and embedded into the slider 21 along the U-shaped groove 211 of the slider 21, and then the outer shell 313 is rotated clockwise until the limiting boss 3132 on the outer shell 313 abuts against the lower end surface of the ¼ circular groove 213 of the slider 21. At this moment, the annular shoulder 3131 on the outer shell 313 is screwed into the C-shaped groove 212 on the slider 21, so that the electrode is constrained on the slider 21, and the degrees of freedom in other directions are limited except for the rotation of the outer shell 313 as an axis. After mounted and fixed in the endoscope 40, referring to FIG. 3, the electrode can only move back and forth along the slider 21.

In the process of dismounting the electrode, the outer shell 313 of the binding post 31 is first rotated counterclockwise until the limiting boss 3132 on the outer shell 313 abuts against another end surface of the ¼ circular groove 213 of the slider 21. At this moment, the annular shoulder 3131 on the outer shell 313 is screwed out from the C-shaped groove 212 on the slider 21 and then the binding post 31 is detached from the slider 21 along the U-shaped groove 211. At this moment, the constraint between the electrode and the operating handle is released, thereby separating the electrode from the endoscope to complete the dismounting.

The outer shell 313 of the binding post 31 may be rotated forwardly and reversely. The outer shell 313 has a bayonet, may be fixed on the slider 21 for locking and positioning the electrode, and can also be easily separated from the slider 21.

The distal end of the operating handle is a handle locking head 27. The handle locking head 27 is used to latch with the proximal end of the inner sheath 50. An outer sheath is sleeved outside the inner sheath 50. The proximal end 26 of the operating handle is used to connect the proximal end of the endoscope 40, and the distal end of the endoscope 40 extends toward the electrode 10. A sealing plug 28 is arranged between the proximal end of the inner sheath 50 and the handle locking head 27 to play a sealing role.

Figure 7:
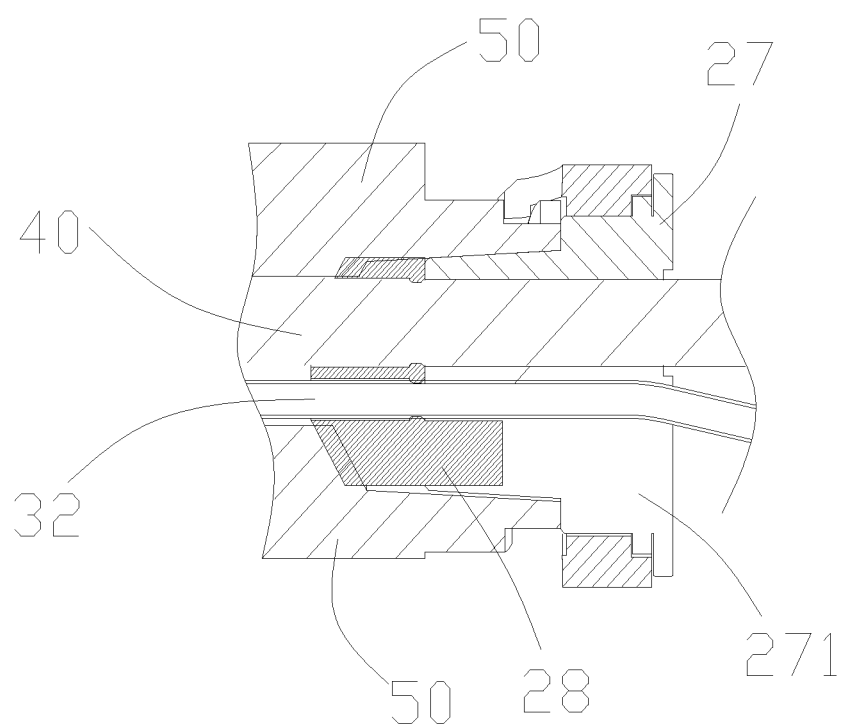
FIG. 7 is a cross-sectional view of a joint between an inner sheath, a sealing plug and a handle locking head.

Specifically, as shown in FIG. 7, the sealing plug 28 is made of a soft elastic material, and the sealing plug 28 is cylindrical. The sealing plug is provided with two through holes in the axial direction. Each through hole is used for allowing the rod portion of the endoscope 40 and the electrode rod 32 of the electrode 10 to pass through. The proximal end of the inner sheath 50 is provided with a limiting surface for abutting against the distal end of the sealing plug 28. The side wall of the proximal end of the inner sheath 50 wraps the sealing plug 28 and is in locked connection with the handle locking head 27. The proximal end of the sealing plug 28 abuts against the handle locking head 27. The sealing plug 28 and the inner sheath are in interference fit, after the proximal end of the inner sheath and the handle locking head are tightly connected, the sealing plug is compressed and deformed and closely fits an inner wall of the proximal end of the inner sheath, and there is no clearance therebetween.

The bottom surface of the sealing plug 28 is further provided with a protrusion 281. The protrusion 281 is used to insert into an original notch 271 on the side wall of the handle locking head 27 to achieve the circumferential positioning of the sealing plug 28, thereby improving the stability and tightness of the sealing plug 28.

Before the electrode and the operating handle are connected, the sealing plug 28 is sleeved on the electrode rod 32. When the electrode and the operating handle are connected, a rod portion of the endoscope 40 passes through another through hole. After the inner sheath is mounted, the sealing plug 28 is compressed by the proximal end of the inner sheath and the handle locking head 27 to realize the sealing function between the inner sheath and the handle.

The above embodiments are only used to illustrate the technical solutions of the present invention without limitation. Although the present invention has been described in detail with reference to the preferred embodiments, those skilled in the art should understand that the technical solutions of the present invention can be modified or equivalently replaced without departing from the purpose and scope of the technical solution, and they should be covered by the scope of the claims of the present invention.

What is claimed is:

1. A resectoscope operating handle and electrode fitting structure, comprising a slider (21) of a resectoscope operating handle and a binding post (31) of an electrode, wherein
the slider (21) has a front surface and a back surface, the front surface of the slider (21) is provided with a mounting groove for mounting the binding post (31); an end surface of the binding post (31) is perpendicular to the front surface of the slider (21); and the binding post (31) is mounted in the mounting groove, and an axial direction of the binding post (31) is perpendicular to a plane where the handle is located;
the mounting groove is a U-shaped groove (211), an opening of the U-shaped groove (211) penetrates a left side surface of the slider (21), a lower portion of the U-shaped groove (211) has a notch penetrating the slider (21), an inner groove wall of the U-shaped groove (211) is provided with a C-shaped groove (212) concaved inwardly, and an arc-shaped groove is provided at an intersection of the lower right of the inner groove wall of the U-shaped groove (211) and the front surface of the slider (21);
the slider (21) is fixed to one end of a connecting bridge of the resectoscope operating handle;
the binding post (31) comprises a post cover (311), an inner shell (312) and an outer shell (313), the post cover (311) is connected to the bottom of the inner shell (312), the outer shell (313) is sleeved outside the inner shell (312), the outer shell (313) and the inner shell (312) form a housing assembly, the housing assembly is provided with a first limiting mechanism for limiting the axial movement of the outer shell (313) and the inner shell (312) and a second limiting mechanism for limiting the circumferential rotation of the inner shell (312), and the outer shell (313) is rotatable forwardly and reversely around the inner shell (312);
an annular shoulder (3131) is arranged at the bottom of the outer shell (313), and the annular shoulder (3131) is provided with a limiting boss (3132) protruding outward; and
an end portion of the binding post (31) is perpendicular to the front surface of the slider (21), the binding post (31) can be embedded in the slider (21) along the U-shaped groove (211), when the outer shell (313) is rotated, the limiting boss (3132) can abut against a lower end surface of the arc-shaped groove, and the annular shoulder (3131) can be screwed into the C-shaped groove (212).

2. The resectoscope operating handle and electrode fitting structure according to claim 1, wherein the arc-shaped groove is a ¼ circular groove (213).

3. The resectoscope operating handle and electrode fitting structure according to claim 1, wherein the first limiting mechanism comprises an annular rib (3121) arranged on an outer wall of the inner shell (312).

4. The resectoscope operating handle and electrode fitting structure according to claim 3, wherein the second limiting mechanism comprises a positioning protrusion (3122) arranged on the top of the inner shell (312) and extending along the axial direction of the inner shell (312), and a positioning hole provided on a top inner wall of the outer shell (313) and corresponding to the positioning protrusion (3122).

5. The resectoscope operating handle and electrode fitting structure according to claim 1, wherein the bottom of the inner shell (312) is provided with a base having an annular protrusion, and the annular shoulder (3131) abuts against an upper end of the base.

6. The resectoscope operating handle and electrode fitting structure according to claim 1, wherein opposite sides of the outer shell (313) have mutually parallel planes (34), and the planes (34) extend from a top end of the outer shell (313) to a bottom end of the annular shoulder (3131).

7. The resectoscope operating handle and electrode fitting structure according to claim 1, wherein the electrode comprises a binding post (31), an electrode rod (32) and a high-frequency connecting wire (33), the high-frequency connecting wire (33) is welded to the electrode rod (32) and fixed in the inner shell (312), the inner shell (312) is filled with epoxy resin glue, the post cover (311) seals the inner shell (312), and the outer shell (313) is sleeved and fixed on the inner shell (312).

8. The resectoscope operating handle and electrode fitting structure according to claim 1, wherein the fitting structure further comprises a sealing plug (28) made of a soft elastic material, a distal end of the operating handle has a handle locking head (27) for being fixed with a proximal end of an inner sheath (50), a proximal end of the operating handle is used to connect a proximal end of a rod portion of an endoscope (40), a distal end of the rod portion of the endoscope (40) extends in the direction of the electrode, and the sealing plug (28) is arranged between the proximal end of the inner sheath (50) and the handle locking head(27).

9. The resectoscope operating handle and electrode fitting structure according to claim 8, wherein the sealing plug (28) is cylindrical, the sealing plug (28) is provided with two through holes in the axial direction, each through hole is used for allowing the rod portion of the endoscope (40) and the electrode rod (32) of the electrode to pass through, the proximal end of the inner sheath (50) is provided with a limiting surface for abutting against a distal end of the sealing plug (28), a side wall of the proximal end of the inner sheath (50) wraps the sealing plug (28) and is fixedly connected to the handle locking head(27), and a proximal end of the sealing plug (28) abuts against the handle locking head(27).

10. The resectoscope operating handle and electrode fitting structure according to claim 9, wherein the sealing plug (28) and the inner sheath (50) are in interference fit, and after the proximal end of the inner sheath (50) and the handle locking head (27) are tightly connected, the sealing plug (28) is compressed and deformed and closely fits an inner wall of the proximal end of the inner sheath (50).

11. The resectoscope operating handle and electrode fitting structure according to claim 10, wherein the bottom surface of the sealing plug (28) is further provided with a protrusion (281), and the protrusion (281) can be inserted into a notch (271) on a side wall of the handle locking head (27) and can circumferentially position the sealing plug (28).

12. A method for mounting and dismounting resectoscope operating handle and electrode fitting structure according to claim 1, comprising the following steps:
  A, during mounting, pushing an end portion of a binding post (31) to an inner end of a U-shaped groove (211) along the U-shaped groove (211), and then rotating an outer shell (313) of the binding post (31) clockwise until the outer shell cannot be rotated, so that an electrode and a slider (21) are locked; and
  B, during dismounting, rotating the outer shell (313) of the binding post (31) counterclockwise until the outer shell cannot be rotated, and pushing out the binding post (31) along the U-shaped groove (211), so that the constraint between the electrode and the slider (21) is released.

* * * * *